(12) United States Patent
Barth et al.

(10) Patent No.: US 9,079,963 B2
(45) Date of Patent: Jul. 14, 2015

(54) MONOCLONAL ANTIBODY FOR THE DETECTION OF SNAP/CLIP TAG

(71) Applicant: Fraunhofer-Gesellschaft zur Förderung der angewandten Forschung e.V., Munich (DE)

(72) Inventors: Stefan Barth, Munich (DE); Katharina Kolberg, Munich (DE); Christiane Püttmann, Munich (DE); Severin Schmies, Munich (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 14/358,628

(22) PCT Filed: Nov. 26, 2012

(86) PCT No.: PCT/EP2012/073608
§ 371 (c)(1),
(2) Date: May 15, 2014

(87) PCT Pub. No.: WO2013/076304
PCT Pub. Date: May 30, 2013

(65) Prior Publication Data
US 2014/0329253 A1   Nov. 6, 2014

(30) Foreign Application Priority Data
Nov. 25, 2011 (EP) ..................... 11190787

(51) Int. Cl.
*C07K 16/40* (2006.01)
*C12N 15/13* (2006.01)
*G01N 33/573* (2006.01)
*G01N 33/58* (2006.01)

(52) U.S. Cl.
CPC .............. *C07K 16/40* (2013.01); *G01N 33/573* (2013.01); *G01N 33/581* (2013.01); *C07K 2317/565* (2013.01); *G01N 2333/91011* (2013.01)

(58) Field of Classification Search
CPC ..... C07K 16/40; G01N 33/581; G01N 33/573
See application file for complete search history.

(56) References Cited

U.S. PATENT DOCUMENTS

| | | | |
|---|---|---|---|
| 5,407,804 A * | 4/1995 | Yarosh | 435/7.4 |
| 5,817,514 A * | 10/1998 | Li et al. | 435/338 |
| 7,888,090 B2 * | 2/2011 | Barnikow et al. | 435/193 |
| 2006/0205027 A1 * | 9/2006 | King et al. | 435/15 |
| 2014/0010829 A1 * | 1/2014 | Bigner et al. | 424/183.1 |

FOREIGN PATENT DOCUMENTS

WO   WO-2009/114748 A1   9/2009

OTHER PUBLICATIONS

Brent et al., 1990. Immunoaffinity purification of human O6-alkylguanine-DNA alkyltransferase using newly developed monoclonal antibodies. Cancer Res. 50: 58-61.*
Gautier et al., 2008. An engineered protein tag for multiprotein labeling in living cells. Chemistry & Biology 15: 128-136.*
Gronemeyer et al., 2006. Directe3d evolution of O6-alkylguanine-DNA alkyltransferase for applications in protein labeling. Protein Engineering, Design & Selection 19: 309-316.*
Keppler et al., 2003. A general method for the covalent labeling of fusion proteins with small molecules in vivo. Nature Biotechnology 21: 86-89.*
Pegg et al., 1991. Production of antibodies to peptide sequences present in human O6-alkylguanine-DNA alkyltransferase and their use to detect this protein in cell extracts. Carcinogenesis 12: 1671-1677.*
Von Wronski et al., 1991. Structural and Immunological comparison of indigenous human O6-methylguanine-DNA methyltransferase with that encoded by a cloned DNA. J. Biol. Chem. 266(2): 1064-1070.*
Von Wronski et al., 1994. Effect of 5-azacytidine on expression of the human DNA repair enzyme O6-methylguanine-DNA methyltransferase. Carcinogenesis 15(4): 577-582.*
Score Sequence Alignments, US20140010829 SEQ ID No. 14 and 18 with instant SEQ ID No. 7 and 6, respectively.*
Sequence Listing, WO 2009/11478, SEQ ID Nos. 87 and 88.*
Ward et al., "Ligand-induced internalization of the orexin $OX_1$ and cannabinoid $CB_1$ receptors assessed via N-terminal SNAP and CLIP-tagging", British Journal of Pharmacology, vol. 162, 2011, p. 1439-1452.
Yamamoto et al., "Ultrastructural localization of stage-specific neurite-associated protiens in the developing rat cerebral and cerebellar cortices", Journal of Neurocytology, vol. 19, No. 5, 1990, p. 619-627.
International Search Report and Written Opinion in Application No. PCT/EP2012/073608 mailed Mar. 1, 2013.
Aliprandi et al., "The Availability of a Recombinant Anti-SNAP Antibody in VHH Format Amplifies the Application Flexibility of SNAP-tagged Proteins", Journal of Biomedicine and Biotechnolgy, vol. 2010, Article ID 658954, 7 pgs. (2010).

* cited by examiner

*Primary Examiner* — Gail R Gabel
*Assistant Examiner* — James L Grun
(74) *Attorney, Agent, or Firm* — Venable, LLP; Therese Finan; Nancy Axelrod

(57) ABSTRACT

A monoclonal antibody that binds specifically to the SNAP motif and to the CLIP tag comprising CDRs with the amino acid sequences SEQ ID Nos. 3, 4, 5, and 8, 9, 10.

7 Claims, 4 Drawing Sheets

Figures 2A, 2B:
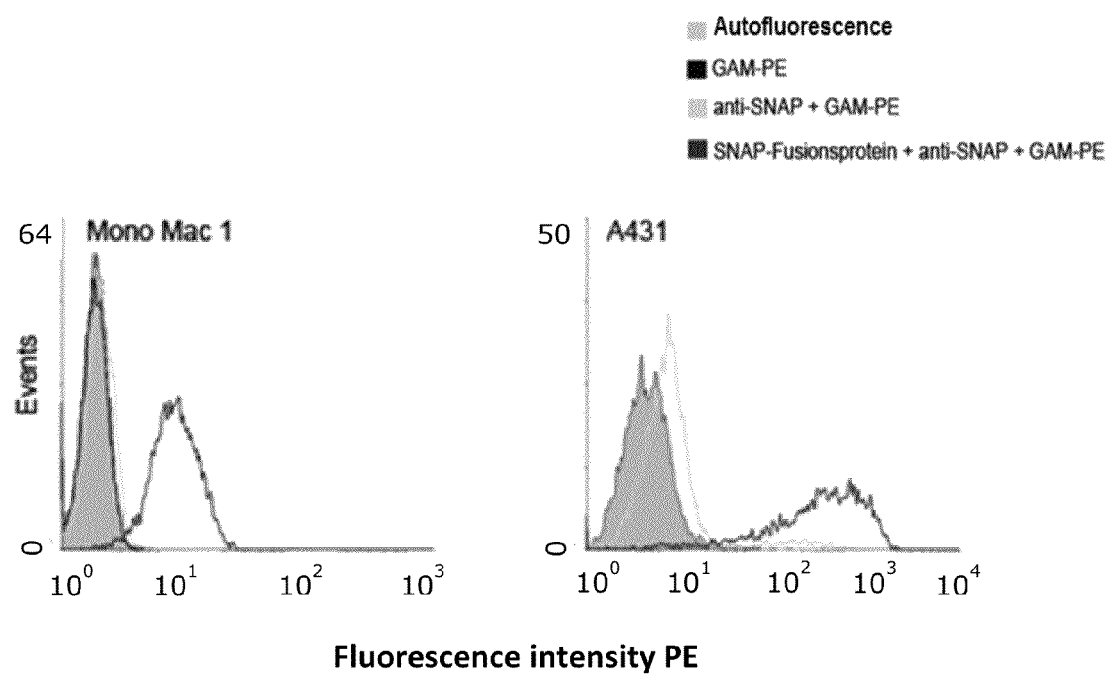

Fig. 1A
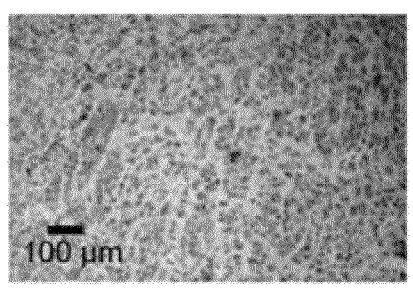
PBS-control
Fig. 1B
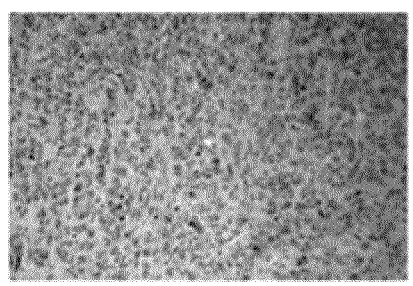
anti-SNAP Ak
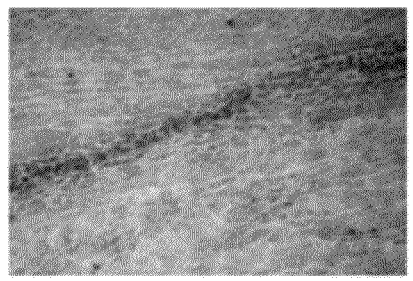
H22-SNAP + anti-SNAP Ak
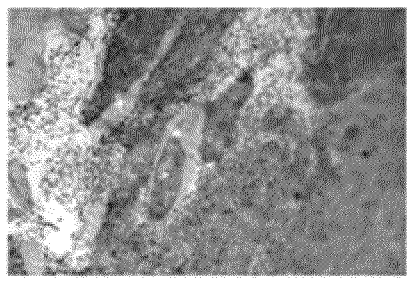
425(scFv)-SNAP + anti-SNAP Ak
Fig. 1C
Fig. 1D

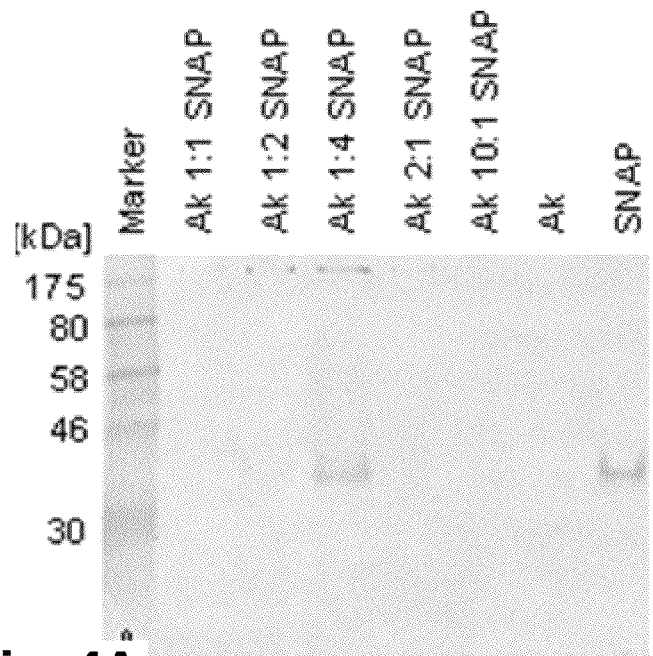
Fig. 4A anti-cMyc-AP
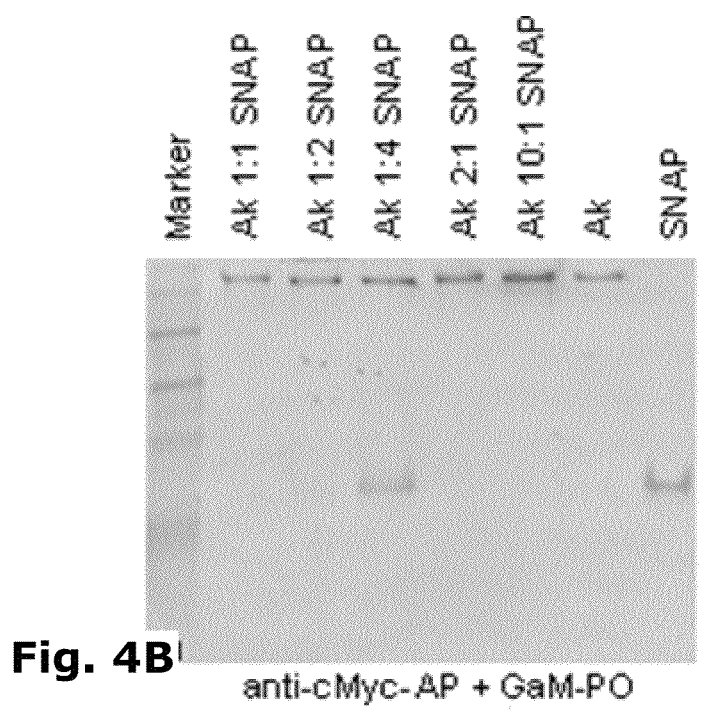
Fig. 4B anti-cMyc-AP + GaM-PO

SEQUENCE LISTING

<160> NUMBER OF SEQ ID NOS: 10

<210> SEQ ID NO 1
<211> LENGTH: 336
<212> TYPE: DNA
<213> ORGANISM: Mouse

<400> SEQUENCE: 1
caggtccaac tgcagcagtc tgggcctgaa ctgatgaggc ctgggacttc agtaaagatg      60
tcctgcaagg cttcaggcta tctcttcacc agttattgga tgcactgggt gaaacagagg     120
cctggacaag gccttgagtg gattgccatg atcgatcctt ccaatagtga gacttggttg     180
aatcagaatt tcaaggacaa ggccacattg aatgtagaca atcctccaa gacagcctac      240 atgcagctca gcaacctgac atctgaggac tctgcagtct attactgtgc aagagggac      300 tactggggcc aaggcaccac tctcacagtc tcctca                               336

<210> SEQ ID NO 2
<211> LENGTH: 112
<212> TYPE: PRT
<213> ORGANISM: Mouse

<400> SEQUENCE: 2

Gln Val Gln Leu Gln Gln Ser Gly Pro Glu Leu Met Arg Pro Gly Thr
1               5                   10                  15

Ser Val Lys Met Ser Cys Lys Ala Ser Gly Tyr Leu Phe Thr Ser Tyr
            20                  25                  30

Trp Met His Trp Val Lys Gln Arg Pro Gly Gln Gly Leu Glu Trp Ile
        35                  40                  45

Ala Met Ile Asp Pro Ser Asn Ser Glu Thr Trp Leu Asn Gln Asn Phe
    50                  55                  60

Lys Asp Lys Ala Thr Leu Asn Val Asp Lys Ser Ser Lys Thr Ala Tyr
65                  70                  75                  80

Met Gln Leu Ser Asn Leu Thr Ser Glu Asp Ser Ala Val Tyr Tyr Cys
                85                  90                  95

Ala Arg Gly Asp Tyr Trp Gly Gln Gly Thr Thr Leu Thr Val Ser Ser
            100                 105                 110

<210> SEQ ID NO 3
<211> LENGTH: 5
<212> TYPE: PRT
<213> ORGANISM: Mouse

<400> SEQUENCE: 3

Ser Tyr Trp Met His
1               5

<210> SEQ ID NO 4
<211> LENGTH: 17
<212> TYPE: PRT
<213> ORGANISM: Mouse

<400> SEQUENCE: 4

Met Ile Asp Pro Ser Asn Ser Glu Thr Trp Leu Asn Gln Asn Phe Lys
1               5                   10                  15

Asp

<210> SEQ ID NO 5
<211> LENGTH: 3
<212> TYPE: PRT

<213> ORGANISM: Mouse

<400> SEQUENCE: 5

Gly Asp Tyr
1

<210> SEQ ID NO 6
<211> LENGTH: 330
<212> TYPE: DNA
<213> ORGANISM: Mouse

<400> SEQUENCE: 6

```
gacattgtgc tgacacagtc tcctgcttcc ttagctgtat ctctggggca gagggccacc    60
atctcataca gggccagcaa aagtgtcagt acatctggct atagttatat gcactggaac   120
caacagaaac caggacagcc acccagactc ctcatctatc ttgtatccaa cctagaatct   180
ggggtccctg ccaggttcag tggcagtggg tctgggacag acttcaccct caacatccat   240
cctgtggagg aggaggatgc tgcaacctat tactgtcagc acattaggga gcttacgttc   300
ggaggggga ccaagctgga aatcaaacgt                                      330
```

<210> SEQ ID NO 7
<211> LENGTH: 110
<212> TYPE: PRT
<213> ORGANISM: Mouse

<400> SEQUENCE: 7

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
                20                  25                  30

Gly Tyr Ser Tyr Met His Trp Asn Gln Gln Lys Pro Gly Gln Pro Pro
            35                  40                  45

Arg Leu Leu Ile Tyr Leu Val Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Phe Gly Gly Gly Thr Lys Leu Glu Ile Lys Arg
                100                 105                 110

<210> SEQ ID NO 8
<211> LENGTH: 15
<212> TYPE: PRT
<213> ORGANISM: Mouse

<400> SEQUENCE: 8

Arg Ala Ser Lys Ser Val Ser Thr Ser Gly Tyr Ser Tyr Met His
1               5                   10                  15

<210> SEQ ID NO 9
<211> LENGTH: 7
<212> TYPE: PRT
<213> ORGANISM: Mouse

<400> SEQUENCE: 9

Leu Val Ser Asn Leu Glu Ser
1               5

-continued

```
<210> SEQ ID NO 10
<211> LENGTH: 7
<212> TYPE: PRT
<213> ORGANISM: Mouse

<400> SEQUENCE: 10

Gln His Ile Arg Glu Leu Thr
1               5
```

MONOCLONAL ANTIBODY FOR THE DETECTION OF SNAP/CLIP TAG

CROSS REFERENCE TO RELATED APPLICATIONS

This application is a National Stage of International Application No. PCT/EP2012/073608, filed Nov. 26, 2012, which claims priority to European Application No. 11190787.9, filed Nov. 23, 2011, both of which are hereby incorporated by reference in their entirety.

The present invention relates to an antibody for the detection of SNAP/CLIP tags, to nucleic acids coding for such an antibody, and to the use of such an antibody for the detection of proteins containing SNAP/CLIP tags.

The SNAP and CLIP tag technology is a relatively young technology. It is an elegant way to provide target proteins, especially fusion proteins, with desired ligands.

WO 20009/114748 A1 discloses SNAP-25 compositions, methods of making α-SNAP-25 antibodies that bind an epitope comprising a carboxyl-terminus at the P1 residue from the BoNT/A cleavage site scissile bond from a SNAP-25 cleavage product, α-SNAP-25 antibodies that bind an epitope comprising a carboxyl-terminus at the P1 residue from the BoNT/A cleavage site scissile bond from a SNAP-25 cleavage product, methods of detecting BoNT/A activity, and methods of detecting neutralizing α-BoNT/A antibodies.

M. Yamamoto, L. Hassinger, J. E. Crandall report in Journal of Neurocytology 19, 619-627 (1990) about ultrastructural localization of stage-specific neurite-associated proteins in the developing rat cerebral and cerebellar cortices. SNAP/TAG-1 is a glycoprotein of 135 kDa and is expressed on the surface of a subset of growing axons in the developing rodent CNS. The ultrastructural localization of this antigen was analysed in embryonic day 17 cerebral cortex and postnatal days 4 and 8 cerebellar cortex of rats using immunoelectron microscopy with a monoclonal antibody which recognizes SNAP/TAG-1 (4D7), and peroxidase-conjugated secondary antibody. In the embryonic cortex, immunoreactivity was associated with the plasma membranes of restricted groups of axons, neuronal somata and their leading processes located in the intermediate zone, subplate and cortical plate. Immunoreactive axons were bundled together in groups of 10-20 and were separated from non-immunoreactive axons. Some growth cones were immunoreactive; however, not all growth cones of 4D7-immunoreactive axons showed staining. In the postnatal cerebellum, immunoreactivity was associated with the somata and axons of granule cells that are located in the most internal portion of the external granule cell layer. In cerebral and cerebellar cortices, immunoreactivity appeared in corresponding points of adjacent cell membranes in punctuate fashion and with a regular periodicity of 100-200 nm. The possibility that SNAP/TAG-1 is acting as an adhesion molecule among specific subgroups of axons in the developing CNS is discussed.

Richard J Ward, John D Pediani, and Graeme Milligan report in British Journal Pharmacology (2011), 162, 1439-1452 about Ligand-induced internalization of the orexin $OX_1$ and cannabinoid $CB_1$ receptors assessed via N-terminal SNAP and CLIP-tagging. Cell surface forms of each receptor construct were detected by both antibody recognition of the epitope tags and covalent binding of fluorophores to the $O^6$-alkylguanine-DNA-alkyltransferase variants. Receptor internalization in response to agonists but not antagonists could be monitored by each approach but sensitivity was up to six- to 10-fold greater than other approaches when employing a novel, time-resolved fluorescence probe for the SNAP tag. Sensitivity was not enhanced, however, for the CLIP tag, possibly due to higher levels of nonspecific binding.

The SNAP tag is based on the human DNA repair enzyme O(6)-alkylguanine DNA alkyltransferase. The latter has been altered by introducing mutations to such an extent that a protein variant having a smaller molecular size and extremely high affinity for benzylguanine could be selected. The SNAP tag undergoes a highly specific reaction with benzylguanine derivatives, binding the benzyl radical with the substrate coupled thereto covalently to itself with cleavage of guanine. As a recombinant protein tag, it enables the covalent and stoichiometrically defined coupling of various benzylguanine-modified substrates to the fusion protein. The CLIP tag was developed from the SNAP tag by mutagenesis and undergoes a highly specific reaction with benzylcytosine derivatives rather than benzylguanine. Thus, the simultaneous differentiated labeling of SNAP and CLIP tags in one experimental approach is possible. The SNAP technology (SNAP/CLIP plasmids and substrates) is distributed by New England Biolabs (NEB).

In "Journal of Biomedicine and Biotechnology", Vol. 2010, Article ID658954, doi: 10.1155/2010/658954, Aliprandi et al. disclose a recombinant anti-SNAP antibody in a VHH format.

It is desirable to have an analytical tool by which both CLIP and SNAP tags can be detected.

The object of the invention is achieved by the antibody according to claim 1. The monoclonal antibody of the invention that binds specifically to the SNAP tag motif and to the CLIP tag and comprises CDRs with the amino acid sequences SEQ ID Nos. 3, 4, 5, and 8, 9, 10. In particular, the antibody of the invention is a murine antibody.

Subject matter of the invention is also a nucleic acid coding for the antibody of the invention, in particular a nucleic acid having the nucleic acid sequence of SEQ ID Nos. 1 or 6.

The antibody of the invention is obtainable by a process of the invention, in which an immunization is effected by means of a SNAP tag protein in non-human mammals, especially mice, and hybridoma cells are obtained therefrom, from which the antibody cell lines that recognize both the SNAP and the CLIP tags are identified by binding assays.

Also the use of the antibody of the invention for the detection of both a SNAP and CLIP tag Aliprandi et al. describe a recombinant antibody that recognizes the SNAP tag. The antibody according to the invention can be used for staining tissue sections. The murine anti-SNAP antibody according to the present invention can be used, in particular, for staining cryosections and paraffin sections. An advantage of the antibody according to the invention over the antibody already published in Aliprandi et al. is its greater valence; the recombinant protein can recognize only one epitope, while the antibody according to the invention can recognize two epitopes.

FIGS. 1A-1D: Immunohistochemistry; staining of cryosections of an A431 tumor obtained from mice with HAI SNAP (anti-EGFR) and M2D11. FIG. 1A: PBS-control. FIG. 1B: anti-SNAP Ak. FIG. 1C: H22-SNAP+anti-SNAP Ak. FIG. 1D: 425(scFv)-SNAP+anti-SNAP Ak.

FIGS. 2A-2B: Flow cytometry; FIGS. 2A, 2B show the binding of M2D11 to two different SNAP fusion proteins in flow cytometry. FIG. 2A: MonoMac1. FIG. 2B: A431.

Figure 3A:
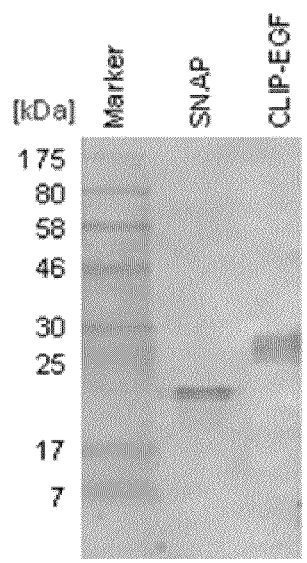
Figure 3B:
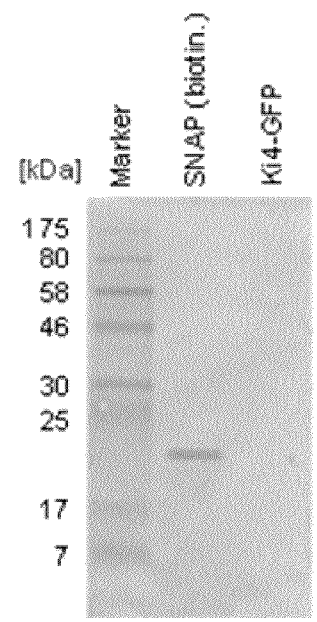
Figure 3C:
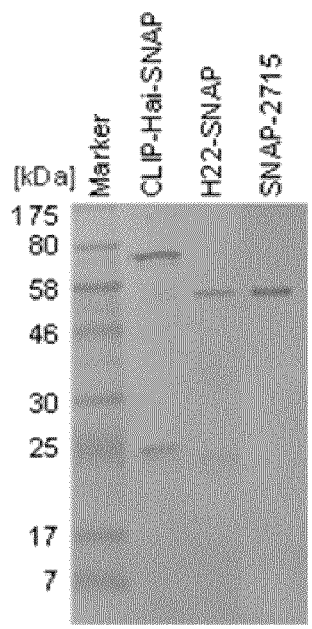

FIGS. 3A-3C: Western blot analysis; FIGS. 3A-3C show, on the one hand, the binding of M2D11 to the two proteins SNAP and CLIP-EGF in a denaturing gel. FIG. 3A: Lanes 2 and 3 show SNAP and CLIP-EGF, respectively. FIG. 3B: Lanes 2 and 3 show SNAP (biotin) and Ki4-GFP, respectively. FIG. 3C: Lanes 2, 3 and 4 show CLIP-Hai-SNAP, H22-SNAP and SNAP-2715, respectively.

FIGS. 4A-4B: Western blot analysis; FIG. 4 shows the blot of a native polyacrylamide gel for detecting the binding of M2D11 and SNAP protein in solution. FIG. 4A shows Anti-cMyc-AP. FIG. 4B shows Anti-cMyc-AP+GaM-PO.

The antibody according to the invention is able to detect both the SNAP tag and the CLIP tag. The antibody according to the invention has the advantage that the SNAP fusion proteins can be detected in flow cytometry. The sensitivity of the antibody in ELISA (enzyme-linked immunosorbent assay) and Western blot is similar to that of the antibody described by Aliprandi et al.

In addition to the methods described, the antibody according to the invention was tested in immunohistochemical experiments. It can be employed for the detection of SNAP fusion proteins in cryosections and in paraffin sections.

In a specific embodiment, the antibody is a monoclonal antibody. In particular, the antibody may be of murine origin. The murine antibody is advantageous because murine IgG antibodies belong to the most frequently employed antibody formats in molecular-biological research. Thus, the work with such antibodies and the detection of murine IgG antibodies is familiar to the skilled persons in many laboratories.

The heavy chain variable region of the antibody according to the invention is shown in SEQ ID No. 2, and SEQ ID No. 1 relates to the nucleic acid coding for this region.

The light chain variable region of the antibody according to the invention is shown in SEQ ID No. 7, and SEQ ID No. 6 relates to the nucleic acid coding for this region.

CDRs of the heavy chain of the antibody according to the invention are listed in amino acid sequences SEQ ID Nos. 3-5. CDRs of the light chain of the antibody according to the invention are listed in amino acid sequences SEQ ID Nos. 8-10.

The invention also relates to nucleic acids coding for the mentioned proteins, especially SEQ ID Nos. 1 and 6.

The present invention also relates to a process for preparing the antibody according to the invention, in which an immunization is effected by means of a SNAP tag protein in non-human mammals, especially mice. From these, hybridoma cell lines are obtained, and the antibody cell lines that recognize both the SNAP and the CLIP tags are identified by corresponding binding assays.

The antibodies according to the invention can be used for the detection of SNAP and CLIP tags individually, but also of a combination thereof.

EXAMPLE

Polyacrylamide Gel Electrophoresis and Western Blot

The samples to be analyzed were denatured in Laemmli buffer (or in a native sample buffer without SDS) and electrophoresed on a 12% (w/v) SDS polyacrylamide gel and a polyacrylamide gel (160 V, 60 min). The proteins were visualized by Coomassie staining or transferred to a nitrocellulose membrane (Whatman, Schleicher & Schuell, Dassel, Germany) (350 mA, 70 min). After the transfer, the membrane was blocked at room temperature in 1% (w/v) BSA for 1 hour. After washing three times in PBS-T, the blot was incubated with the primary antibody (1 hour). After three further washing steps, the specific binding was detected with an enzyme-conjugated secondary antibody (1 hour) and the corresponding substrate (10 min). In the analysis of SNAP or CLIP proteins, the samples were incubated with BG or BC substrates before denaturing. The results are shown in FIG. 3.

FIGS. 3A-3C: Western blot analysis. FIGS. 3A, 3B and 3C show, on the one hand, the binding of M2D11 to the two proteins SNAP and CLIP EGF in a denaturing gel. The antibody shows no cross-reactivity with other His6-tagged proteins (GFP-Ki4). In addition, FIG. 3B shows that the antibody does not compete with the SNAP substrate for the binding to SNAP. After biotinylation of the SNAP protein with BG biotin, the protein can further be detected with M2D11. In addition, FIG. 3C shows the binding of the antibody to different SNAP-scFv fusions (H22-SNAP, SNAP-2715) and to CLIP-scFv-SNAP fusion proteins.

FIGS. 4A-4B: Western blot analysis. FIGS. 4A, 4B show the blot of a native polyacrylamide gel for detecting the binding of M2D11 and SNAP protein in solution. FIG. 4A shows the existence of SNAP protein through the Myc tag of the protein. It becomes clear that the protein is bound by M2D11 also in solution, and that free protein is detectable only at an excess of 1:4. In FIG. 4B, antibody was additionally detected, so that a colocalization of both proteins could be shown.

Immunohistochemistry

The tissue sections were prepared from EGFR-positive subcutaneous tumors originating from BALB/c mice with A-431 tumors (DSMZ No. ACC 91). After sacrificing the animals, the tumors were embedded in "Jung tissue freezing medium" (Leica Microsystems, Nussloch, Germany) and frozen in liquid nitrogen. Cryosections of 8 µm were prepared with a Leica 3050S Kryostat and dried over night. The sections were fixed in acetone for 10 min, dried and outlined with an Immunopen (Sigma Aldrich). The tumor cells were stained with an EGFR-specific scFv fusion protein 425scFv SNAP (0.034 mg/ml) as a primary antibody. After three washes in PBST, the SNAP fusion protein was detected with different concentrations of the peroxidase-labeled antibody M2D11 (stock solution: 657 ng/µl). Both antibody incubation steps were performed at room temperature for 45 min, and the washing steps were performed with shaking at room temperature for 5 min. After two washes in PBST and one wash in TBST, the tissue sections were incubated in 3-amino-9-ethylcarbazole (AEC) solution until staining became visible. Subsequently, counterstaining was performed with haematoxylin before the sections were mounted in glycerol gel. The results are shown in FIG. 1.

FIGS. 1A-1D: Immunohistochemistry. Staining of cryosections of an A431 tumor obtained from mice with 425 (scFv)-SNAP (anti-EGFR) and M2D11. FIG. 1A: PBS-control. FIG. 1B: anti-SNAP Ak. FIG. 1C: H22-SNAP+anti-SNAP Ak. FIG. 1D: 425*scFv)-SNAP+anti-SNAP Ak.

Flow Cytometry

The functionality of M2D11 was analyzed by flow cytometry with FACSCalibur (Becton & Dickinson) and CellQuest software. The non-specific binding to the cell surface of different cell lines was detected, as was the specific binding of SNAP fusion proteins bound to the cell. About $4*10^5$ cells were incubated first in 100 µl of PBS with 1-2 µg of SNAP/CLIP fusion protein and then in 100 µl of PBS with 3.3 ng of M2D11 on ice for 30 min. For detection, the cells were incubated with GaM-PE (1:100, Dianova, Hamburg, Germany) on ice for 30 min. The cells were then analyzed by flow cytometry. The PBS washing steps were performed in a standard cell wash centrifuge between all steps. The cells were resuspended in 300 µl of PBS for the measurement. The results are shown in FIG. 2.

FIGS. 2A-2B: Flow cytometry. FIGS. 2A, 2B show the binding of M2D11 to two different SNAP fusion proteins in flow cytometry. On both cell lines, no or only very little cross-reactivity of the antibody with the cell surface can be detected. Mono Mac 1 and A431 cells are shown here by way of example. FIG. 2A: MonoMac1. FIG. 2B: A431. The analyses were additionally performed with cell lines PC-3, CHO-K1, Kasumi, Mcf-7, L3.6pl, L540 and FG.

The invention claimed is:

1. A monoclonal antibody that binds specifically to a SNAP tag motif and to a CLIP tag, wherein the heavy chain of the monoclonal antibody comprises, situated in the orientation from the N-terminus to the C-terminus, complementarity determining regions (CDRs) with the amino acid sequences SEQ ID Nos. 3, 4, 5, respectively, and the light chain of the antibody comprises, situated in the orientation from the N-terminus to the C-terminus, CDRs with the amino acid sequences SEQ ID Nos. 8, 9, 10, respectively.

2. The antibody according to claim 1, which is a murine antibody.

3. The monoclonal antibody of claim 1 comprising the amino acid sequences represented by SEQ ID Nos. 2 and 7.

4. An isolated nucleic acid coding for the antibody according to claim 1.

5. The isolated nucleic acid according to claim 4, having the nucleic acid sequence represented by SEQ ID Nos. 1 and 6.

6. An isolated nucleic acid coding for the antibody according to claim 2.

7. The isolated nucleic acid according to claim 6, having the nucleic acid sequence represented by SEQ ID Nos. 1 and 6.

* * * * *